United States Patent [19]

Aufdembrink

[11] Patent Number: 4,831,006
[45] Date of Patent: May 16, 1989

[54] METHOD FOR INTERCALATING ORGANIC-SWELLED LAYERED METAL CHALCOGENIDE WITH POLYMER CHALCOGENIDE BY TREATMENT WITH ORGANIC, HYDROLYZABLE, POLYMERIC CHALCOGENIDE PRECURSOR WHEREIN ORGANIC HYDROLYSIS BY-PRODUCTS ARE REMOVED

[75] Inventor: Brent A. Aufdembrink, Voorhees, N.J.

[73] Assignee: Mobil Oil Corporation, New York, N.Y.

[21] Appl. No.: 140,528

[22] Filed: Jan. 4, 1988

Related U.S. Application Data

[63] Continuation-in-part of Ser. No. 879,787, Jun. 27, 1986, which is a continuation-in-part of Ser. No. 687,414, Dec. 28, 1984, abandoned.

[51] Int. Cl.$^4$ .................. B01J 21/06; B01J 23/20
[52] U.S. Cl. .................................. 502/242; 502/246; 502/525
[58] Field of Search ............... 502/242, 350, 77, 63, 502/80, 246, 525; 423/70, 71

[56] References Cited

U.S. PATENT DOCUMENTS

| | | | |
|---|---|---|---|
| 4,600,503 | 7/1986 | Angevine et al. | 208/251 H |
| 4,650,779 | 3/1987 | Goldstein | 502/38 |

OTHER PUBLICATIONS

U.S. Appln. Ser. No. 687,414, filed 12/28/84 (Atty. Docket No. 3104).
European Pat. Appln. 85309347.4, published 12/30/86.
U.S. Appln. Ser. No. 879,787, filed 6/27/86, (Atty. Docket No. 3946).
PCT/U.S. 87/01447, filed 6/11/87, (Atty. Docket No. 3946-1).
PCT/U.S. 87/01445, filed 6/11/87, (Atty. Docket No. 3946-2).
PCT/U.S. 87/01444, filed 6/11/87, (Atty. Docket No. 3946-3).
PCT/U.S. 87/01443, filed 6/11/87, (Atty. Docket No. 3946-4).
PCT/U.S. 87/01442, filed 6/11/87, (Atty. Docket No. 3946-5).
U.S. Appln. Ser. No. 938.098, filed 12/4/86, Doc. No. 3554.
U.S. Appln. Ser. No. 939,265, filed 12/9/86, Doc. No. 3591.
U.S. Appln. Ser. No. 092,249, filed 9/2/87, (Docket 4285).
U.S. Appln. Ser. No. 755,251, filed 7/15/85 (Docket 3542).
U.S. Appln. Ser. No. 023,345, filed 3/9/87 (Docket 4230).
U.S. Appln. Ser. No. 026,426, filed 3/16/87 (Docket 4191S).
U.S. Appln. Ser. No. 884,934, filed 7/14/86 (Docket No. 4051N).
U.S. Appln. Ser. No. 104,630, filed 10/5/87 (Docket 4491).
U.S. Appln. Ser. No. 028,813, filed 3/23/87 (Docket 4251S).
U.S. Appln. Ser. No. 128,124, filed 12/3/87 (Docket 4577).

Primary Examiner—Carl F. Dees
Attorney, Agent, or Firm—Alexander J. McKillop; Charles J. Speciale; Edward F. Kenehan, Jr.

[57] ABSTRACT

Organic-swelled layered metal chalcogenides, e.g., titanometallates or silicotitanates, are intercalated with polymeric chalcogenide, e.g., polymeric silica by treatment with organic hydrolyzable polymeric chalcogenide precursor wherein hydrolysis to polymeric chalcogenide is enhanced by removal of organic hydrolysis by-products, during hydrolysis, e.g., by exposure of the reaction mixture to elevated temperatures.

31 Claims, No Drawings

METHOD FOR INTERCALATING ORGANIC-SWELLED LAYERED METAL CHALCOGENIDE WITH POLYMER CHALCOGENIDE BY TREATMENT WITH ORGANIC, HYDROLYZABLE, POLYMERIC CHALCOGENIDE PRECURSOR WHEREIN ORGANIC HYDROLYSIS BY-PRODUCTS ARE REMOVED

This application is a continuation-in-part of U.S. application Ser. No. 879,787, filed June 27, 1986 which is a continuation-in-part of U.S. application Ser. No. 687,414, filed Dec. 28, 1984 (now abandoned), the entire contents of both being incorporated herein by reference.

The present invention relates to a method for preparing layered metal chalcogenides containing interspathic polymeric chalcogenides. In one aspect, the invention relates to layered metal oxides which contain interspathic metal oxides, e.g., layered titanium oxides which contain interspathic silica. For the purposes of the invention, the term "metal" can be considered to include the elements boron, silicon, phosphorus and arsenic.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

Various approaches have been taken to provide layered materials of enhanced interlayer distance having thermal stability. Most techniques rely upon the introduction of an inorganic "pillaring" agent between the layers of a layered material.

Layered metal chalcogenide materials enjoying thermal stability can be prepared by a method described in U.S. application Ser. No. 879,787, filed June 27, 1986, and incorporated herein by reference. The method comprises: treating a layered chalcogenide, e.g., oxide, of at least one element having an atomic number of 4, 5, 12 to 15, 20 to 33, 38 to 51, 56 to 83 and greater than 90, inclusive, which contains ion exchange sites having interspathic cations associated therewith, with an organic compound which is a cationic species, e.g., n-alkylammonium or capable of forming a cationic species e.g., n-alkylamine, to effect exchange with said interspathic cations in order to swell the layered material. An electrically neutral compound capable of conversion to an interspathic polymeric chalcogenide, e.g., tetraethylorthosilicate, is therafter provided between the layers of the swelled, layered chalcogenide. The compound is then converted to the interspathic polymeric chalcogenide to form the layered material, e.g. by hydrolysis.

In the past, such layered materials have been prepared by a process wherein an organic-swelled layered material is contacted with the electrically neutral organic compound capable of conversion by hydrolysis to polymeric chalcogenide to form a pillared product under ambient temperatures and pressures. Moreover, it has been found that certain organic-swelled layered materials, such as perovshite-related layered metal oxides, are impossible or difficult to intercalate by this procedure. Moreover, such materials often require extended times for effecting conversion to the polymeric chalcogenide, and yet the resulting pillared product exhibits only modest sorption capacity and surface area after calcination.

It has now been found that layered materials containing an interspathic, i.e., intercalated, polymeric chalcogenide can be prepared even from layered materials which have been difficult to treat by conventional techniques. The method comprises intercalating an organic-swelled layered metal chalcogenide with a polymeric chalcogenide by a method which comprises (a) providing between the layers of said organic-swelled layered metal chalcogenide an organic, hydrolyzable, polymeric chalcogenide precursor compound capable of conversion to said polymeric chalcogenic by hydrolysis and (b) converting said compound to an interspathic polymeric chalcogenide in a reaction system under conditions which facilitate faster removal of organic hydrolysis by-products from the reaction system than occurs under ambient conditions, i.e., room temperature and atmospheric pressure.

In one embodiment of the present invention, said converting is effected in the presence of water. Preferably, water is added to the reaction system after setp (a) has been completed.

After conversion to the polymeric chalcogenide the resulting product shows increased surface area and increased sorption capacity for water and $C_6$ hydrocarbons. While not wishing to be bound by theory, it is believed that carrying out hydrolysis of the precursor under conditions which facilitate removal of organic hydrolysis by-products provides an enhanced driving force for hydrolysis. Moreover, when such conditions include increased temperatures, it is believed that the rate of hydrolysisis is further enhanced by increased kinetic energy.

For present purposes, polymeric chalcogenides are considered to include chalcogenides of two or more repeating units, preferably three or more repeating units, say four or more or even five or more repeating units. The extent of polymerization of the interspathic polymeric chalcogenide is believed to affect the ultimate interlayer separation of the pillard layered metal oxide product.

The layered chalcogenide material which is organic-swelled to form the organic-swelled starting material employed in the present invention can be a layered oxide, sulfide, selenide or telluride, preferably a layered oxide material of elements other than those of Group VIB of the Periodic Table, i.e., O, S, etc. Suitable layered oxide materials include layered oxides of Group IVA metals such as titanium, zirconium and hafnium, e.g., layered trititanates, such as $Na_2Ti_3O_7$ comprising $Ti_3O_7^{-2}$ layers containing interspathic alkali metals as disclosed in U.S. Pat. Nos. 4,600,503, and 2,496,993 incorporated herein by reference. Upon intercalation wtih polymeric silica, such tritanates are known as silicotitanates. Other layered chalcogenide materials in which the present invention may be used to facilitate intercalation include $KTiNbO_5$, as well as layered oxides of alumina and silicon such as clays, e.g. bentonite. In particular, the present invention can facilitate intercalation of layered silicates known as high silica alkali silicates whose layers lack octahedral sheets. These silicates can be prepared hydrothermally from an aqueous reaction mixture containing silica and caustic at relatively moderate temperatures and pressures, and may contain tetracoordinate framework atoms other than Si. Included among these materials are magadiite, natrosilite, kenyaite, makatite, nekoite, kanemite, okenite, dehayelite, macdonaldite and rhodesite, preferably their acid-exchanged forms.

Another layered chalcogenide which can be pillared by the present invention is a titanometallate-type layered metal oxide product comprising a layered metal oxide wherein each layer of the metal oxide has the general formula

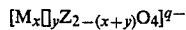

$$[M_x\square_yZ_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $q=4y-x(n-4)$ and preferably is 0.6–0.9,
$0<x+y<2$.

Interposed between the layers of the oxide will be charge-balancing cations A of charge m wherein m is an integer between 1 and 3, preferably 1. Preferably A is a large alkali metal cation selected from the group consisting of Cs, Rb, K, M and Na is a divalent or trivalent metal cation selected from at least one Mg, Sc, Mn, Fe, Cr, Ni, Cu, Zn, In, Ga and Al. For example, M can be both In and Ga. Structurally, these metal oxides are believed to consist of layers of (M, Z, or $\square$) $O_6$ octahedra which are trans edge-shared in one dimension and cis edge-shared in the second dimension forming double octahedral layers which are separated by cations in the third dimension. These materials can be prepared by high temperature fusion of a mixture of (1) metal oxide, (2) alkali metal carbonate or nitrate and (3) tetravalent metal dioxide, e.g., titanium dioxide or by fusion of a mixture of alkali metallate and tetravalent metal dioxide. Such fusion can be carried out in air in ceramic crucibles at temperatures ranging between 600° to 1100° C. after the reagents have been ground to an homogeneous mixture. The resulting product is ground to 20 to 250 mesh, preferably about 100 mesh, prior to the organic swelling and polymeric oxide intercalation steps.

Further description of layered titanometallate starting materials and their methods of preparation can be found in the following references:

Reid, A.F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough, J. B.; Wiseman, P. J. *J. Solid State Chem.* 1983, 49 300.

Use of these layered metal oxides as the layered starting material permits inclusion of different metal atoms into the layered starting material being treated which allows potential catalytically active sites to be incorporated in the stable layer itself. Moreover, variable amounts of metal atoms may be added to provide a catalyst with optimum activity for a particular process. Furthermore, the infinite trans-edge shared layer structure of the titanometallates-type layered metal oxides instead of the sheared 3-block structure of, for example, $Na_2Ti_3O_7$, may reduce or eliminate shearing of the layers as a possible mechanism for thermal or hydrothermal decomposition of the calcined intercalated material. These titanometallate-type materials may possess even greater thermal stability than silicotitanate molecular sieves. In addition, the variable charge density on the oxide layer possible for these layered metal oxides due to the various oxidation states of metal oxides, the incorporated metal atom and the varying stoichiometry of the materials, may allow variation in the amount of the organic cationic species which can be exchanged into the material. This, in turn, permits variation of the ultimate concentration of the oxide pillars between the layers of the final product.

The metal oxide product contains about 0.5 to about 20 weight percent of said element M, preferably about 1 to 10 weight percent. Vacancy-containing materials (wherein y is greater than zero) are particularly suited for treatment by the percent method.

The titanometallate-type layered metal oxide product, after intercalation with polymeric chalcogenide the present invention comprises a layered titanometallate-type layered metal oxide and interspathic polymeric chalcogenide of at least one element, separating the layers of the metal oxide. Preferably, such materials after pillaring are thermally stable, i.e., capable of withstanding calcination at a temperature of about 450° C. for at least 2 hours without significant reduction (e.g., not greater than 10 or 20%) in the spacing between the layers.

The method of the present invention may also be used in preparing thermally stable layered materials containing interspathic polymeric chalcogenides where the layered material is a perovskite-related layered oxide. Perovskite-related layered oxides are known in the art and are described, for example by Dion, M; Ganne, M., Tournoux, M; in *Mat. Res. Bull,* 1981, 16, 1429. These materials as well as their organic-swelled analogues, e.g., those which are octylamine-swelled, are disclosed in U.S. Pat. No. 4,593,013. Such materials can be treated by the method of the present invention to incorporate interspathic polymeric chalcogenides therein. Both of these references are incorporated herein by reference. See also, Structure Properties and Preparation of Perovskite Type Compounds by F. Galasso, Pergamon Press, 1969, and Jacobson et al, *Inorg. Chem*, 1985, 24, 3727, both of which are incorporated herein by reference.

The perovskite-related layered-oxides used herein may be represented by the formula $M_m[A_{n-1}B_nO_{3n+1}]$ wherein M is a charge-balancing interspathic cation. $[A_{n-1}B_nO_{3n+1}]$ represents a perovskite-like layer wherein A is one more metal atoms capable of occupying 12-coordinate sites, B is a metal atom capable of occupying 6-coordinates sites, m is greater than 0, preferably less than or equal to 1 and n is greater than or equal to 2, preferably 3 is less than or equal to n is less than or equal to 7. Each layer comprises a cubic arrangement of corner-shared $BO_6$ octahedral with A occupying a 12-coordinated site in the center of each cube. For purposes of the present invention, the term "cubic arrangement" can include any generally cubic or pseudo-cubic arrangement.

The thickness of each layer in terms of $BO_6$ octahedra is denoted by n. In other words, the layers can vary, for example, between 3 and 7 $BO_6$ octahedra in thickness, depending on the perovskite-like layered material. Perovskite-like layered materials treated by the method of the present invention preferably have layers of a low charge density in order to exhibit the ion exchange properties necessary for incorporation of the more common propping agents prior to intercalation with polymeric chalcogenide precursor. Although some pereovskite-like layered materials have a charge density per formula unit of two or more, the perovskite-like layered materials treated by the present invention preferably have a charge density of one or less. However, it is possible that propping agent of requisite shape and charge can exchange with the interspathic cations in materials where m is greater than 1.

During preparation of the perovskite-related layered oxide according to the method of the present invention it has been found beneficial to carry out the swelling step utilizing a cationic species or cationic species precursor at temperatures above ambient, say, e.g. 70° to 110° C., say about 100° C. Similarly, the interspathic polymeric chalcogenide precursor is preferably introduced to the layered oxide at temperatures above ambient, e.g. for 70° to 100° C., say about 80° to 90° C. The products thus prepared can be described as a thermally stable composition comprising a perovskite-related layered oxide containing an interspathic polymeric oxide of an element selected from Groups IB, IIB, IIIA, IIIB, IVA, IVB, VA, VB, VIA, VIIA and VIIIA of the Periodic Table, preferably an element selected from Group IVB of the Periodic Table e.g., interspathic polymeric silica. One such composition is comprised of perovskite-like layers represented by the formula $Ca_2Nb_3O_{10}$ containing an interspathic polymeric oxide such as interspathic polymeric silica.

M can be monovalent, divalent or trivalent cation, preferably a monovalent cation selected from the group consisting of Li, Na, K, Rb, Cs, $NH_4$ and H, while A can be one or more mono-, di- or trivalent cations selected from the group consisting of Groups IA, IIA and IIIB and the lanthanides and B can be one or more transition metals selected from Re and Groups IVB, VB and VIB. In one preferred embodiment, $A_{n-1}$ can be $Ca_2Na_{n-3}$ and B is Nb; in other words, the perovskite layer is represented by the formula $Ca_2Na_{n-3}Nb_nO_{3n+1}$. Preferably in such cases, M is K and n is 3, e.g., $KCa_2Nb_3O_{10}$.

The organic swelling agent used to swell the layered starting material employed in the present invention comprises a source of organic cation such as organoammonium, which source may include the cation itself, in order to effect an exchange of the interspathic cations resulting in the layers of the starting material being propped apart. In particular, protonated alkylamines are preferred. Often, alkylammonium cations include M-dodecylammonium, n-octylammonium, n-heptylammonium, n-hexylammonium and n-propylammonium. The source of organic cation in those instances where the interspatahic cations include hydrogen or hydronium ions may include a neutral compound such as organic amine which is converted to a cationic analogue during the swelling or "propping" treatment. Among these materials are $C_3$ to $C_{10}$, preferably $C_6$ to $C_8$ alkylamines, preferably n-alkylamines, or $C_3$ to $C_{10}$, preferably $C_6$ to $C_8$ alkanols, preferably n-alkanols. The present invention has been found particularly useful in pillaring materials which do not contain interspathic alkali metals, e.g., layered materials having ammonium ($NH_4^+$) ions disposed between the layers.

Interspathic polymeric chalcogenide pillars are then formed between the layers of the organic-swollen layered metal chalcogenide starting materials and may include a chalcogenide, preferably a polymeric chalcogenide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable chalcogenides include those of Group VA, e.g., V, Nb, and Ta, those of Group IIA, e.g., Mg or those of Group IIIB, e.g., B. Most preferably, the pillars include polymeric silica. In addition, the chalcogenide pillars may include an element which provides catalytically active acid sites in the pillars, preferably aluminum.

The chalcogenide pillars are formed from a precursor material which is preferably introduced between the layers of the organic "propped" species as a cationic, or more preferably, electrically neutral, hydrolyzable compound of the desired elements, e.g., those of group IVB. The precursor material is preferably an organometallic compound which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Where the pillars are also required to include a different polymeric metal oxide, e.g., alumina or titania, a hydrolyzable compound of said metal can be contacted with the organic "propped" species before, after or simultaneously with the contacting of the propped titanometallate with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used. In addition, the chalcogenide precursor may contain zeolite precursors such that exposure to conversion conditions results in the formation of interspathic zeolite material as at least part of the chalcogenide pillars. Pillars of polymeric silica and polymeric alumina or polymeric silica and polymeric titania are particularly preferred.

After the final hydrolysis to produce the chalcogenide pillars and calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

The resulting pillared products exhibit thermal stability at temperatures of 500° C. or even higher as well as substantial sorption capacities (as much as 10 to 25 wt. % for $H_2O$ and $C_6$ hydrocarbon). Silica-pillared products possess interlayer separations of greater than 12A and surface areas greater that 250 $m^2/g$ when divalent metal atoms, e.g., Mg, Ni, Cu and Zn, are present as the metal M of the product. Silica-pillared products incorporating trivalent metal atoms, e.g., Sc, Mn, Fe, Cr, In, Ga and Al can possess interlayer separations of 6 to 15A.

Layered materials containing interspathic polymeric chalcogenide can be improved when their preparation includes conditions which facilitate removal of organic hydrolysis by-products produced during conversion to polymeric chalcogenides. For example, where tetraalkylorthosilicate is used as the organic precursor, alkanols are produced during hydrolysis. By maintaining temperatures which enhance removal of such alkanols, the rate and extent of hydrolysis are enhanced. Where tetraethylorthosilicate (TEOS) is used, ethanol is a hydrolysis by-product. By conducting polymeric chalcogenide precursor incorporation and hydrolysis at 50° to 170° C., preferably 75° to 85° C., say about 80° C., pillared products having enhanced crystallinity and interlayer spacings are prepared. Moreover, organic hydrolysis by-products removal can be facilitated by conducting hydrolysis in a system which permits removal of the organic hydrolysis by-product from the system. Preferably, such a system contains a means for preventing the introduction of water from outside the system, for example, an outlet tube connected to a silicone fluid bubbler.

The present invention is illustrated further by the following Example. In this example, X-ray diffraction data were obtained by standard techniques using K-alpha doublet of copper radiation.

EXAMPLE

Preparation of Perovskite-Related Layered Oxide $Ca_2Nb_3O_{10}$ Containing Interspathic Polymeric Silica $KCa_2Nb_3O_{10}$ was prepared by reacting a thoroughly ground mixture of 200 g $K_2CO_3$, 69.04 g $CaCO_3$ and 398.36 g $Nb_2O_5$ in a mole ratio of 1:4:3 at 750° C. in air for 6 hours followed by 24 hours of heating at 1149° C. The material was cooled, reground and refired at 1149° C. for 24 hours. 100 g of $KCa_2Nb_3O_{10}$ were then stirred in 300 ml of 6M HCl for 24 hours at 60° C. The resulting solid was cooled, filtered, washed with water and dried overnight resulting in hydrated $HCa_2Nb_3O_{10}$. 30 Grams of this material were stirred in 200 ml of water for 1 hour and 37.25 grams of n-octylamine were then added from a dropping funnel. The resulting mixture was heated to reflux and stirred for 24 hours. The reaction mixture was then filtered, washed with 1500 ml of hot water and dried in air overnight. An x-ray diffraction pattern of the powder from this reaction indicated a layer (d) spacing of 31.5 angstroms. The solid was then stirred in tetraethylorthosilicate (5 g TEOS g/solid) for 72 hours at 80° C. The material was filtered, air dried, and calcined for 4 hours at 500° C. An x-ray diffraction pattern of this powder exhibited a low angle d-spacing of 27.6 angstroms. The thickness of the $Ca_2Nb_3O_{10}$ layer was approximately 12.0 angstroms, leaving an interlayer opening of 15.6 angstroms.

This experiment was duplicated except that TEOS was added at room temperature. No low angle d-spacing was shown by the resulting product indicating that pollaring had not occurred.

I claim:

1. A method for intercalating an organic-swelled layered metal chalcogenide with a polymeric chalcogenide which comprises (a) providing between the layers of said organic-swelled layered metal chalcogenide an organic, hydrolyzable polymeric chalcogenide precursor compound capable of conversion to said polymeric chalcogenide by hydrolysis and (b) converting said compound to an interspathic polymeric chalcogenide in a reaction system under conditions which facilitate faster removal of organic hydrolysis by-products from the reaction system than occurs under ambient conditions.

2. The method of claim 1 wherein said converting is effected in the presence of water.

3. The method of claim 2 wherein water is added to said reaction system after step (a).

4. The method of claim 1 wherein said conditions comprise elevated temperatures which facilitate removal of said organic by-products.

5. The method of claim 4 wherein said temperature ranges from about 50° to 170° C.

6. The method of claim 1 wherein said temperature ranges from about 75° to 85°C.

7. The method of claim 1 wherein the product of (b) is calcined.

8. The method of claim 1 wherein said interspathic polymeric chalcogenide is an interspathic polymeric oxide and said layered metal chalcogenide is a layered oxide.

9. The method of claim 1 wherein said interspathic polymeric oxide comprises polymeric silica.

10. The method of claim 1 wherein said layered metal chalcogenide is a perovskite-related layered oxide.

11. The method of claim 10 wherein said perovskite-related oxide is represented by the formula $M_m[A_{n-1}B_nO_{3n+1}]$ wherein M is a charge-balancing interspathic cation, $[A_{n-1}B_nO_{3n+1}]$ represents a perovskite-like layer, A is one or more metal atoms capable of occupying 12-coordinate sites, B is a metal atom capable of occupying 6-coordinate sites, m is greater than zero, n is greater than or equal to 2 and each layer comprises a cubic arrangement or corner-shared $BO_6$ octahedra with A occupying a 12-coordinated site in the center of each cube.

12. The method of claim 11 wherein m is less than or equal to 1 and 3 is less than or equal to n is less than or equal to 7.

13. The method of claim 12 wherein m=1.

14. The method of claim 11 wherein said layered material is calcined to remove organics.

15. The method of claim 12 wherein said M is a monovalent cation selected from the group consisting of Li, Na, K, Rb, Cs, NH4 and H, A is one or more mono-, di- or trivalent cations selected from the group consisting of Groups IA, IIA, IIIB and the lanthanides, and B is one ore more transition metals selected from Re and Groups IVB, VB and VIB.

16. The method of claim 12 wherein $A_{n-1}$ is $Ca_2$-$Na_{n-3}$ and B is Nb.

17. The method of claim 12 wherein $A_{n-1}$ is $Ca_2$-$Na_{n-3}$ and B is Nb.

18. The method of claim 17 wherein said M is K.

19. The method of claim 11 wherein said perovskite-related layered oxide is $MCa_2Nb_3O_{10}$.

20. The method of claim 1 wherein said layered metal chalcogenide is a titanometallate-type layered metal oxide product comprising a layered metal oxide wherein each layer of the metal oxide has the general formula $$[M_x \square_y Z_{2-(x+y)} O_4]^{q-}$$

wherein M is at least one metal of valence n wherein n is an integer between 0 and 7 and preferably is 2 or 3, 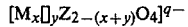 represents a vacancy site, Z is a tetravalent metal, preferably titanium, and wherein $q=4y-x(n-4)$, and $0<x+y<2$.

21. The method of claim 1 wherein said layered metal chalcogenide is a titanate.

22. The method of claim 21 wherein said titanate comprises $Ti_3O_7{}^{-2}$ layers.

23. The method of claim 1 wherein said layered metal chalcogenide is a high silica alkali silicate.

24. The method of claim 23 wherein said silicate is selected from the group consisting of magadiite, natrosilite, kenyaite, makatite, nekoite, kanemite, okenite, dehayelite, macdonaldite and rhodesite.

25. The method of claim 24 wherein said silicate is magadiite.

26. The method of claim 1 wherein said electrically neutral compound is tetraalkylorthosilicate.

27. The method of claim 1 wherein said electrically neutral compound is tetraethylorthosilicate.

28. The method of claim 1 wherein said swelling organic is alkylamine.

29. The method of claim 1 wherein said swelling organic is n-octylamine.

30. The method of claim 1 wherein said swelling organic is alkylammonium.

31. The method of claim 1 wherein said swelling oganic is n-octylammonium.

* * * * *